United States Patent
Sugito et al.

(10) Patent No.: US 7,288,081 B2
(45) Date of Patent: *Oct. 30, 2007

(54) DISPOSABLE WEARING ARTICLE

(75) Inventors: Tomoko Sugito, Kagawa-ken (JP); Yoshio Ono, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/334,534

(22) Filed: Jan. 19, 2006

(65) Prior Publication Data

US 2006/0161127 A1 Jul. 20, 2006

(30) Foreign Application Priority Data

Jan. 19, 2005 (JP) .................. 2005-12078

(51) Int. Cl.
*A61F 13/15* (2006.01)
(52) U.S. Cl. .................. 604/387; 604/391; 604/389
(58) Field of Classification Search ............ 604/387, 604/391
See application file for complete search history.

(56) References Cited

U.S. PATENT DOCUMENTS

| | | | |
|---|---|---|---|
| 6,149,639 A | 11/2000 | Lundberg et al. | |
| 2003/0135190 A1 | 7/2003 | Widlune et al. | |
| 2004/0006327 A1* | 1/2004 | Karami | 604/391 |
| 2004/0236303 A1 | 11/2004 | Igaue et al. | |
| 2005/0177126 A1* | 8/2005 | Kurata | 604/387 |

FOREIGN PATENT DOCUMENTS

| | | |
|---|---|---|
| EP | 1166736 A2 | 1/2002 |
| GB | 2267024 A * | 11/1993 |
| JP | 3059224 | 3/1999 |
| WO | 9530397 | 11/1995 |
| WO | 97/23180 | 7/1997 |
| WO | WO97/36566 * | 10/1997 |
| WO | 00/37010 | 6/2000 |
| WO | 0113843 | 3/2001 |
| WO | 0113845 | 3/2001 |

* cited by examiner

*Primary Examiner*—Tatyana Zalukaeva
*Assistant Examiner*—Ginger T. Chapman
(74) *Attorney, Agent, or Firm*—Lowe Hauptman Ham & Berner LLP

(57) ABSTRACT

In a disposable wearing article, connector sheet strips for connecting front and rear waist regions of the article have proximal sections and flap-like sections. The proximal sections are fixed to the rear waist region on its inner surface along zones contiguous to transversely opposite side edges of the rear waist region. Flexural rigidity of the flap-like sections as measured in a transverse direction of the article is higher than that of the article as measured in regions lying immediately inside the respective zones which are, in turn, contiguous to the respective side edges, so that a direction in which the connector sheet strips extend can be easily reversed.

12 Claims, 7 Drawing Sheets

US 7,288,081 B2

DISPOSABLE WEARING ARTICLE

RELATED APPLICATIONS

The present application is based on, and claims priority from, Japanese Application No. 2005-12078, filed Jan. 19, 2005, the disclosure of which is hereby incorporated by reference herein in its entirety.

BACKGROUND OF THE INVENTION

The present invention relates to a disposable wearing article adapted to be used in the form of, for example, a disposable diaper, a disposable diaper for incontinent patient, a disposable diaper cover or disposable training pants.

As one example of such disposable wearing articles, the disposable diaper having its front and rear waist regions adapted to be connected with each other in releasable and refastenable manner by means of sheet-like fasteners is well known. To be used with such disposable diaper of well known art, an example of such fasteners has one end as viewed in a transverse direction of the diaper is adapted to be permanently attached to any one of the front and rear waist regions in the vicinity of a side edge of this waist region. For example, Japanese Patent Publication No. 3096152 (PATENT DOCUMENT 1) discloses the invention relating to a disposable diaper 100 of this type as illustrated by FIGS. 6 and 7 of the accompanying drawings of this specification. The diaper 100 includes sheet-like fastening strips 106. In the case of this diaper 100 of prior art, transversely opposite side edges 103 of a front waist region 101 are put flat together with transversely opposite side edges 104 of a rear waist region 102, then proximal sections 107 of the respective fastening strips 106 having respective distal sections provided on inner surfaces thereof with anchoring layers 105 are put flat together with the transversely opposite side edges 103 of the front waist region 101 and these portions put flat together in this manner are integrally bonded together to form respective joints 108. The front waist region 101 is provided immediately inside the respective joints 108 with cutoff lines 109a along which the front waist region 101 may be separated from the rear waist region 102. When the diaper 100 can be put on the wearer's body in his or her standing position, the diaper 100 previously formed in the type of pants may be put on the wearer's body without cutting off the front waist region 101 from the rear waist region 102. In this case, it is unnecessary to utilize the fastening strips 106 and these fastening strips 106 may be left fastened to the front waist region 101 by means of the anchoring layers 105 to prevent the diaper 100 from getting out its proper position. When the diaper should be put on the wearer's body being in side lying position or lying face up, the front waist region 101 or the fastening strips 106 may be pulled to tear the diaper 100 along the cutoff lines 109a so that the transversely opposite side edges of the front waist region 101 may be separated from the transversely opposite side edges of the rear waist region 102 to obtain the open-type diaper shown by FIG. 7. After such open-type diaper has been appropriately placed on the wearer's body, the fastening strips 105 may be fastened to selected positions on the front waist region 101 by means of the respective anchoring layers 105.

In the case of this well known diaper 100 disclosed in PATENT DOCUMENT 1, the transversely opposite side edges 103 of the front waist region 101, the transversely opposite side edges 104 of the rear waist region 102 and the proximal sections 107 of the respective fastening strips 107 are put flat and bonded together to form the respective joints 108 while the distal sections of the respective fastening strips 106 carrying on the inner surfaces thereof the anchoring layers 105 extend inward from the respective joints 108 over the front waist region 101 as will be seen in FIG. 6. When it is desired to put such diaper 100 into the form of the open-type diaper, the fastening strips 106 must be turned around so that the respective distal sections carrying thereon the anchoring layers 105 extend outward from the respective joints 108 beyond the transversely opposite side edges 104 of the rear waist region 102 as seen in FIG. 7. However, in view of the manner in which the fastening strips 106 are bonded to the diaper 100 as illustrated by FIG. 6, these fastening strips 106 once having been turned around outward may easily restore the initial positions, i.e., it may be impossible for these fastening strips 106 to maintain the positions thereof illustrated by FIG. 7. To deal with such behavior of the fastening strips 106, if it becomes obvious, a mother intending to put the diaper 100 on the wearer's body must at least temporarily hold the fastening strips 106 to prevent these fastening strips 106 from restoring the initial positions thereof before she can actually put the diaper 100 on the wearer's body. Correspondingly, handling of the diaper 100 may be accompanied with more or less trouble.

SUMMARY OF THE INVENTION

In view of the problem as has been described above, it is a principal object of the present invention to provide a wearing article including a pair of fastening strips attached thereto so as to extend inward from transversely opposite side edges of the article and used to connect front and rear waist regions thereof with each other so improved that these fastening strips can be easily turned around so as to extend outward from the transversely opposite side edges of the article.

The object set forth above is achieved, according to the present invention, by an improvement in the disposable wearing article having a longitudinal direction and a transverse direction orthogonal to each other, the article comprising: a front waist region; a rear waist region; a crotch region; the regions respectively having pairs of side edges opposed to each other in the transverse direction so as to extend in the longitudinal direction and pairs of front and rear ends opposed to each other in the longitudinal direction so as to extend in the transverse direction; one of the front and rear waist regions being provided with connector sheet strips attached thereto in a vicinity of the associated one of the pairs of side edges so as to be fastened to the other waist region in a releasable manner and the one waist region being formed with gathers repetitively undulating in the transverse direction between the associated pair of side edges under contraction of elastic members being stretched in the transverse direction and attached in such stretched state to the one waist region.

The improvement according to the present invention is characterized by that the connector sheet strips respectively comprising proximal sections fixed to the one waist region in the vicinity of the associated pair of side edges on a surface destined to face the wearer's skin and flap-like sections extending inward from the proximal sections and provided on respective surfaces thereof opposed to the inner surface with fastening means adapted to cooperate with an outer surface of the other waist region opposed to the inner surface of the one waist region wherein a flexural rigidity of the flap-like sections as measured in the transverse direction is set to be higher than a flexural rigidity of the article as measured in regions defined immediately inside the proximal sections of the respective connector sheet strips as viewed in the transverse direction and formed with the gathers.

In the disposable wearing article according to the present invention, a flexural rigidity of the flap-like sections as measured in the transverse direction is set to be higher than a flexural rigidity of the article as measured in the regions defined immediately inside the proximal sections of the respective connector sheet strips and formed with the gathers. Such uniquely differentiated flexural rigidity ensures that the regions of the article defined immediately inside the proximal sections of the respective connector sheet strips easily bow in response to turning around outward of the flap-like sections in the transverse direction and allows the flap-like sections to be maintained at the tuned around positions. Consequentially, it is not apprehended that the flap-like sections might extend inward again in the transverse direction and prevent the article from being smoothly put on the wearer's body.

DETAILED DESCRIPTION OF THE PREFERRED EMBODIMENTS

Details of a disposable wearing article according to the present invention will be fully understood from the description given hereunder in reference with the accompanying drawings illustrating disposable diapers as typical embodiment of the present invention.

Figure 1:
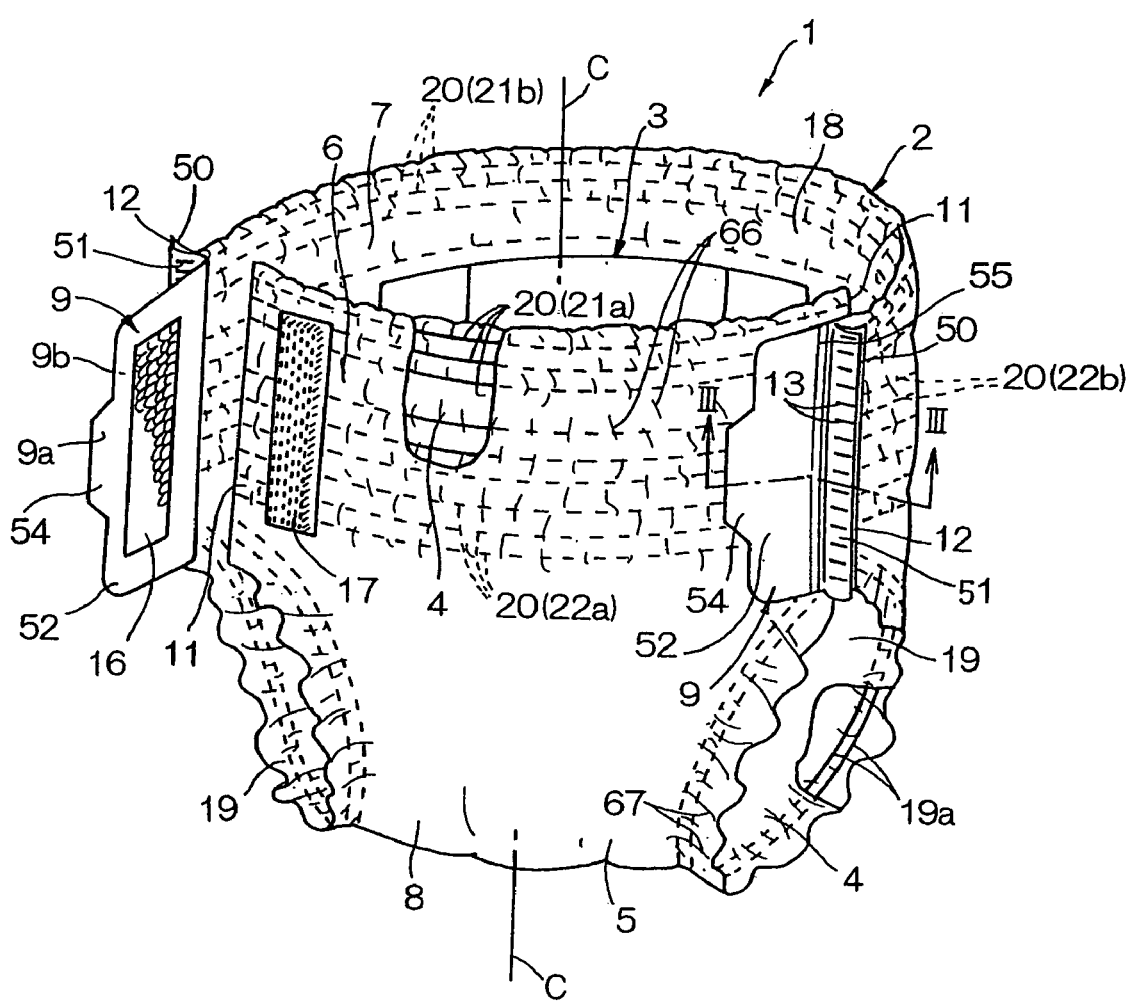
FIG. 1 is a partially cutaway perspective view showing a disposable diaper as a typical embodiment of the present invention with front and rear waist regions connected with each other around the wearer's body.

FIG. 1 is a partially cutaway perspective view showing a disposable diaper 1 for baby generally comprising a chassis 2 and a bodily fluid absorbent panel 3 as the diaper 1 put on the wearer's body. The chassis 2 has a crotch region 8, a front waist region 6 defined in front of the crotch region 8 and a rear waist region 7 defined behind the crotch region 8. These regions 6, 7, 8 are respectively formed by a first sheet, i.e., an outer sheet 5 facing clothes (not shown) of the diaper wearer and a second sheet, i.e., an inner sheet 4 lying on the opposite side of the outer sheet 5 and facing the wearer's skin (not shown). The rear waist region 7 is provided on transversely opposite zones 50 defined immediately inside transversely opposite side edges 12 with connector sheet strips 9 each comprising a third sheet prepared separately of the inner and outer sheets 4, 5. Specifically, these connector sheet strips 9 are put flat and bonded together with the inner sheet 4 so as to form the above-defined zones 50 at a plurality of bonding spots 13 arranged intermittently in the vertical direction as viewed in FIG. 1 along the respective zones 50. Each of the connector sheet strips 9 is relatively long in the vertical direction as viewed in FIG. 1 and has inner and outer surfaces 9a, 9b. A loop member 16 constituting a mechanical fastener widely known in various trade names such as Magic Tape is attached to the inner surface 9a using appropriate adhesive or welding technique. The front waist region 6 is provided in the vicinity of transversely opposite side edges 11 with a hook member 17 constituting the mechanical fastener. Specifically, the hook member 17 is attached to the outer sheet 5 using appropriate adhesive or welding technique. In this way, the loop members 16 cooperate with the hook members 17 to function as fastening means so that the front waist region 6 and the rear waist region 7 may be connected with each other in releasable manner by means of the connector sheet strips 9 as these loop and hook members 16, 17 are placed upon each other. It should be noted here that FIG. 1 shows the front and rear waist regions 6, 7 connected with each other on the right hand but still not connected with each other on the left hand. Upon complete connection of the front and rear waist regions 6, 7 with each other, the diaper 1 is formed with a waist-hole 18 and a pair of leg-holes 19.

Each of the connector sheet strips 9 comprises a proximal section 51 fixed to the associated zone 50 of the rear waist region 7 and a deformable flap-like section 52 extending inward as viewed in the transverse direction from the proximal section 51 toward a center line C-C bisecting a width of the front waist region 6. With respect to the connector sheet strip 9 on the right hand in FIG. 1, the proximal section 51 bonded integrally to the associated zone 50 projects outward from the diaper 1 and the flap-like section 52 extends inward from the proximal section 51 in the transverse direction of the front waist region 6. A distal end of the flap-like section 52 defines a finger-grip 54.

The diaper 1 further includes a plurality of waist elastic members 20 extending in a circumferential direction of the waist-hole 18 and a plurality of leg elastic members 19a extending in a circumferential direction of the respective leg-holes 19. Contraction of these elastic members causes the chassis 2 to form gathers 66, 67 extending in a direction orthogonal to these elastic members 20, 19a, respectively, and repetitively undulating along these elastic members 20, 19a, respectively. In other words, the gathers 66 repetitively undulate in the transverse direction indicated by a double-headed arrow X of the diaper 1 while the gathers 67 repetitively undulate in the circumferential direction of the respective leg-holes 19.

Figure 2:
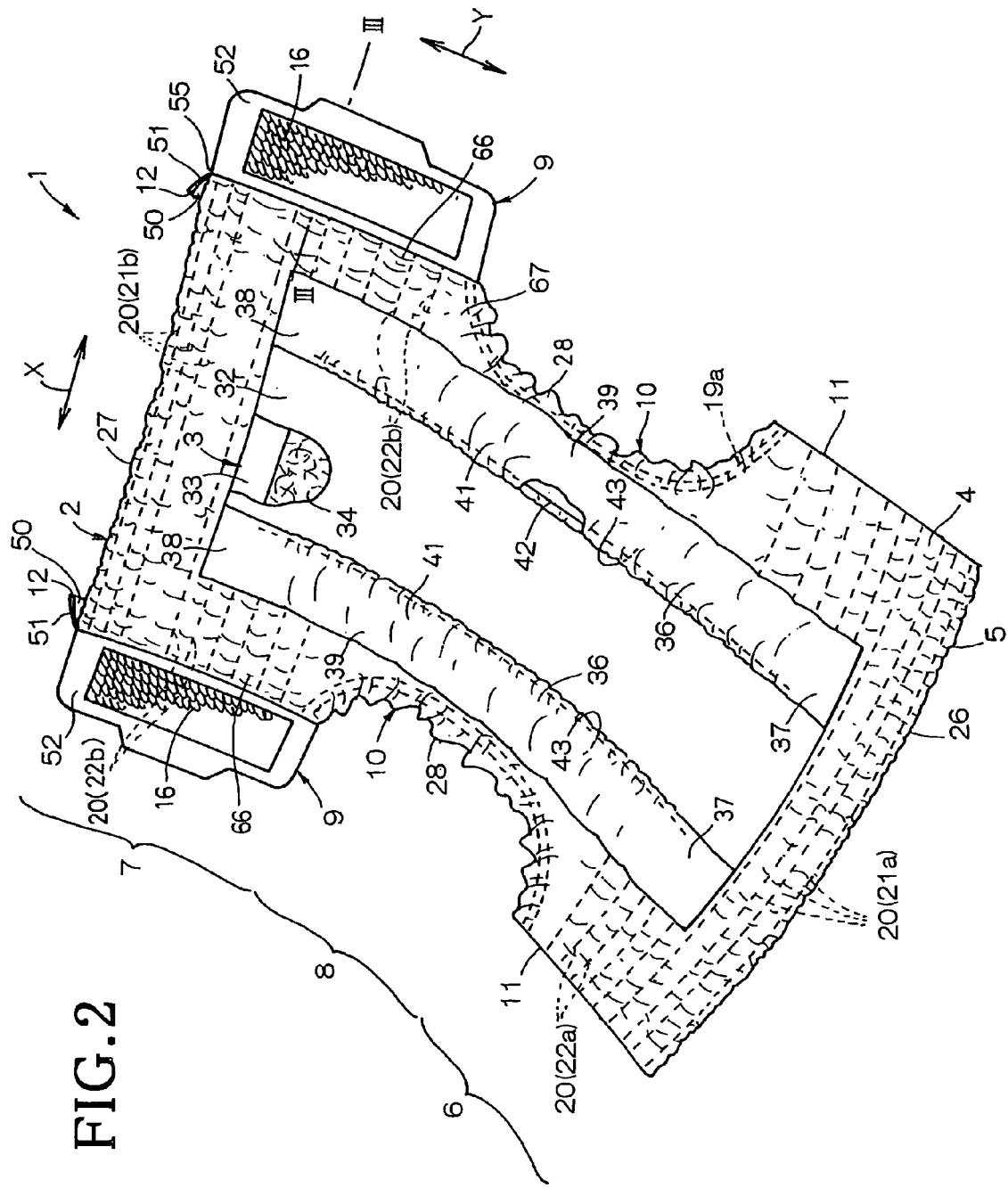
FIG. 2 is a partially cutaway perspective view showing the disposable diaper developed in a transverse direction as well as in a longitudinal direction.

FIG. 2 is a partially cutaway perspective view showing the diaper 1 of FIG. 1 with the front and rear waist regions 6, 7 disconnected from each other and developed in the transverse direction indicated by the double-headed arrow X as well as in the longitudinal direction indicated by a double-headed arrow Y which is orthogonal to the direction of the double-headed arrow X insomuch as the gathers 66, 67 do not completely disappear. The direction X corresponds also to a direction of a waist line. The chassis 2 has a pair of transversely opposite side edges 10 extending in the longitudinal direction. Transversely opposite side edges 10 includes a front pair of edges 11 defined by transversely opposite side edges of the front waist region 6 and a rear pair of transversely opposite side edges 12 defined by transversely opposite side edges of the rear waist region 7. A width between the front pair of transversely opposite side edges 11 is narrower than a width between the rear pair of transversely opposite side edges 12. Of the transversely opposite side edges 10, a central pair of transversely opposite side edges 28 defined by transversely opposite side edges of the crotch region 8 curve from the outside to the inside of the chassis 2 so as to describe circular arcs. The waist elastic members 20 attached in stretched state to the chassis 2 so as to extend along a front end 26 and a rear end 27. The waist elastic members 20 comprise at least a single first elastic member 21a for the front waist region 6 extending in stretched state between the front pair of side edges 11, 11 and at least a single first elastic member 21b for the rear waist region 7 extending in stretched state between the rear pair of rear side edges. The waist elastic members 20 further comprise a plurality of second elastic members 22a for the front waist region 6 and a plurality of second elastic members 22b for the rear waist region 7 both pairs laid below the respective first elastic members 21a, 21b and above the central pair of side edges 28 of the crotch region 8 so as to extend in stretched state between the front pair of side edges 11, 11 and between the rear pair of side edges 12, 12, respectively. In a preferred diaper 1, the respective first elastic members 21a, 21b having a stretch stress higher than that of the respective second elastic members 22a, 22b in order to ensure that the respective first elastic members 21a, 21b are held in contact with the wearer's waist more tightly than the respective second elastic members 22a, 22b are. It is possible for the diaper 1 to use elastic members exhibiting an identical stretch stress as the respective first elastic members 21a, 21b as well as the respective second elastic members 22a, 22b or to use elastic members exhibiting stretch stresses different from each other as the respective first elastic members 21a, 21b or to use elastic members exhibiting stretch stresses different from each other as the respective second elastic members 22a, 22b. It is also possible for the diaper 1 to dispense with the second elastic members 22a and/or the second elastic members 22b. The leg elastic members 19a are attached in stretched state to the chassis 2 along the central pair of side edges 28 of the crotch region 8. These waist elastic members 20 and leg elastic members 19a are sandwiched between the inner and outer sheets 4, 5 and intermittently bonded to at least one, preferably to both of these inner and outer sheets 4, 5. The connector sheet strips 9 have the proximal sections 51 fixed to the zones 50 defined immediately inside the rear pair of side edges 12 and the flap-like sections 52 extending from the inside to the outside of the diaper 1 as viewed in the transverse direction X.

The bodily fluid absorbent panel 3 comprises a liquid-pervious topsheet 32, a liquid-impervious backsheet 33 and a bodily fluid absorbent core 34 sandwiched between these two sheets 32, 33. The top- and backsheets 32, 33 have portions extending outward beyond a peripheral edge of the core 34, these portions being put flat and bonded together using appropriate adhesive or welding technique. Such bodily fluid absorbent panel 3 is provided along transversely opposites with a pair of leak-proof barriers 36 preferably made of liquid-impervious sheets. Each of the leak-proof barriers 36 is bonded to the topsheet 32 at front and rear end sections 37, 38 and along an outer side edge 39 but left free from the topsheet 32 so far as an inner side edge 41 is concerned. To this inner side edge 41, an elastic member 42 extending in the longitudinal direction Y is attached in stretched state. The leak-proof barriers 36 constructed in such manner effectively form a pair of pockets 43 adapted to receive bodily fluid moving on the topsheet 32 in the transverse direction. The backsheet 33 of the bodily fluid absorbent panel 3 is bonded to the inner sheet 4 of the chassis 2 by means of hot melt adhesive (not shown).

In the case of such diaper 1, both the inner sheet 4 and the outer sheet 5 are formed by nonwoven fabric, film or composite sheet consisting of these nonwoven fabric and film laminated one upon another, in any case, preferably containing therein thermoplastic polymer as essential ingredient. The topsheet 32 of the bodily fluid absorbent panel 3 is formed by nonwoven fabric, perforated film or the like made of thermoplastic polymer. The backsheet 33 is formed by film, nonwoven fabric, composite sheet consisting of these film and nonwoven fabric laminated one upon another, or the like. The core 34 is formed by fluff pulp, a mixture of fluff pulp and super-absorbent polymer particles, or the like, in any case, compressed to a desired thickness and preferably wrapped with sheet material having high liquid-permeability and high liquid-diffusivity such as tissue paper. The connector sheet strip 9 is formed by nonwoven fabric or film, composite sheet consisting of these nonwoven fabric and film laminated one upon another, or the like, in any case, preferably containing therein thermoplastic polymer as essential ingredient. A preferred connector sheet strip 9 has a basis weight in a range of 15 to 200 $g/m^2$.

Figure 3:
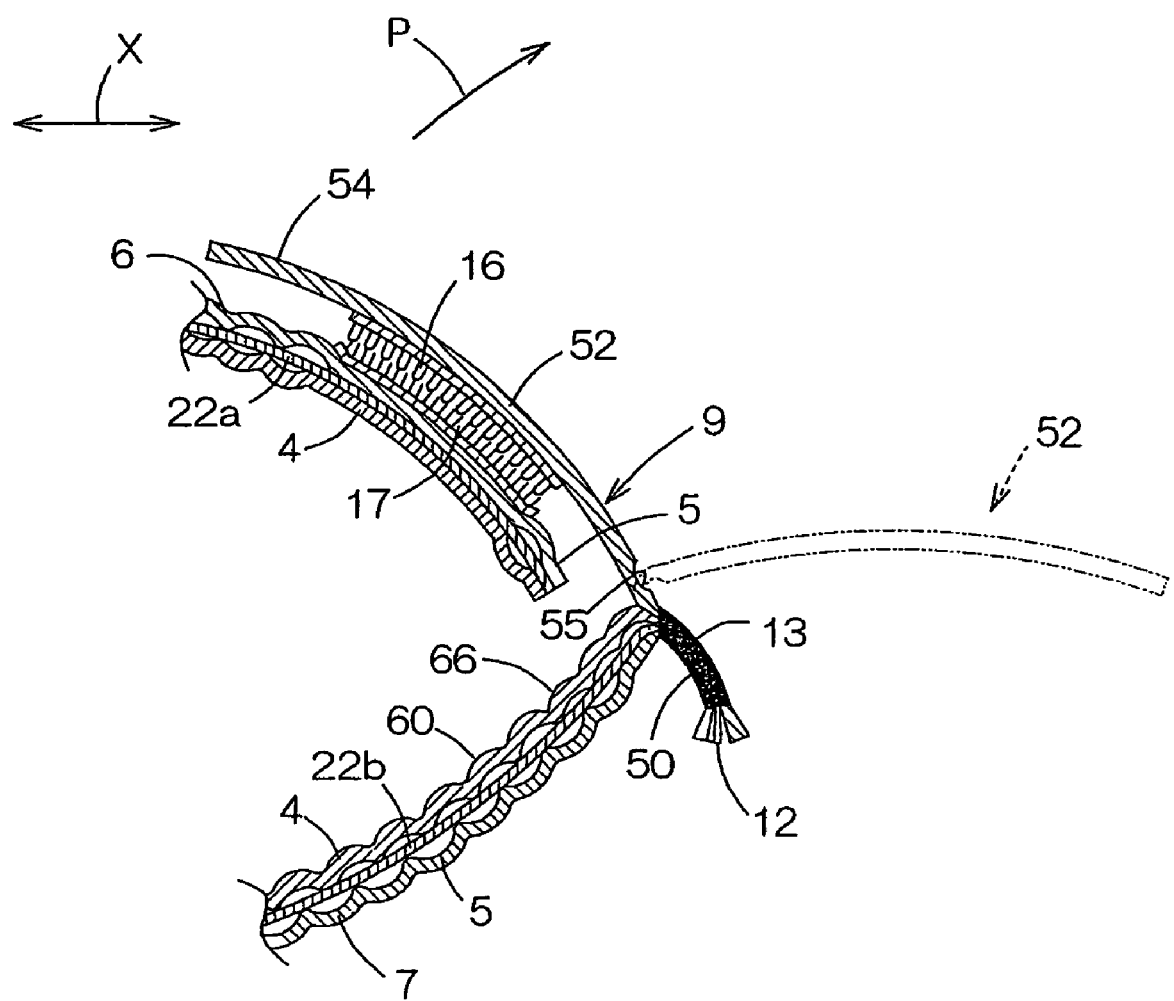
FIG. 3 is a sectional view taken along the line III-III in FIG. 1.

FIG. 3 is a sectional view taken along a line III-III in FIG. 1 wherein the line III-III extends across one of the zones 50 including the bonding spots 13 in parallel to the second elastic members 22a as will be seen in FIG. 1. Preferred bonding spots 13 are formed by thermoplastic polymer contained in any one of the inner sheet 4, the outer sheet 5 and the connector sheet strip 9 as these three sheet materials 4, 5 and 9 are heated under a pressure. More specifically, during this process, the thermoplastic polymer is molten and then solidified to weld these three sheet materials. In this way, the film-like bonding spots 13 are formed. Alternatively, the bonding spots 13 may be formed also by bonding the inner sheet 4, the outer sheet 5 and the connector sheet strip 9 together, for example, using hot melt adhesive or, instead of arranging the bonding spots 13 arranged intermittently in the vertical direction as viewed in FIG. 1, these bonding spots 19 may be implemented in the other manners, for example, so as to extend in the vertical direction as viewed in FIG. 1 in parallel to the rear pair of side edges 12. As will be apparent from FIG. 3, longitudinally opposite ends of the second elastic members 22b for the rear waist region as well as longitudinally opposite ends (not shown) of the first elastic member 21b for the rear waist region extend into the zones 50 defined immediately inside the rear pair of side edges 12 in which the bonding spots 13 are formed. In regions 60 defined immediate inside the respective zones 50, the rear waist region 7 is formed with the gathers 66 along these zones 50 (See FIG. 2).

In the connector sheet strip 9 shown by FIG. 3, the flap-like section 52 extends inward from the one of the zones 50 of the rear waist region 7 toward the inside of the diaper 1 as viewed in the transverse direction. From this state, the flap-like section 52 may be pulled with the finger-grip 54 held by the fingers so as to be rotated in a direction indicated by an arrow P to disengage the loop member 16 on the flap-like section 52 from the hook member 17 on the front waist region 6 and thereby to disconnect the rear waist region 7 from the front waist region 6.

Figure 4:
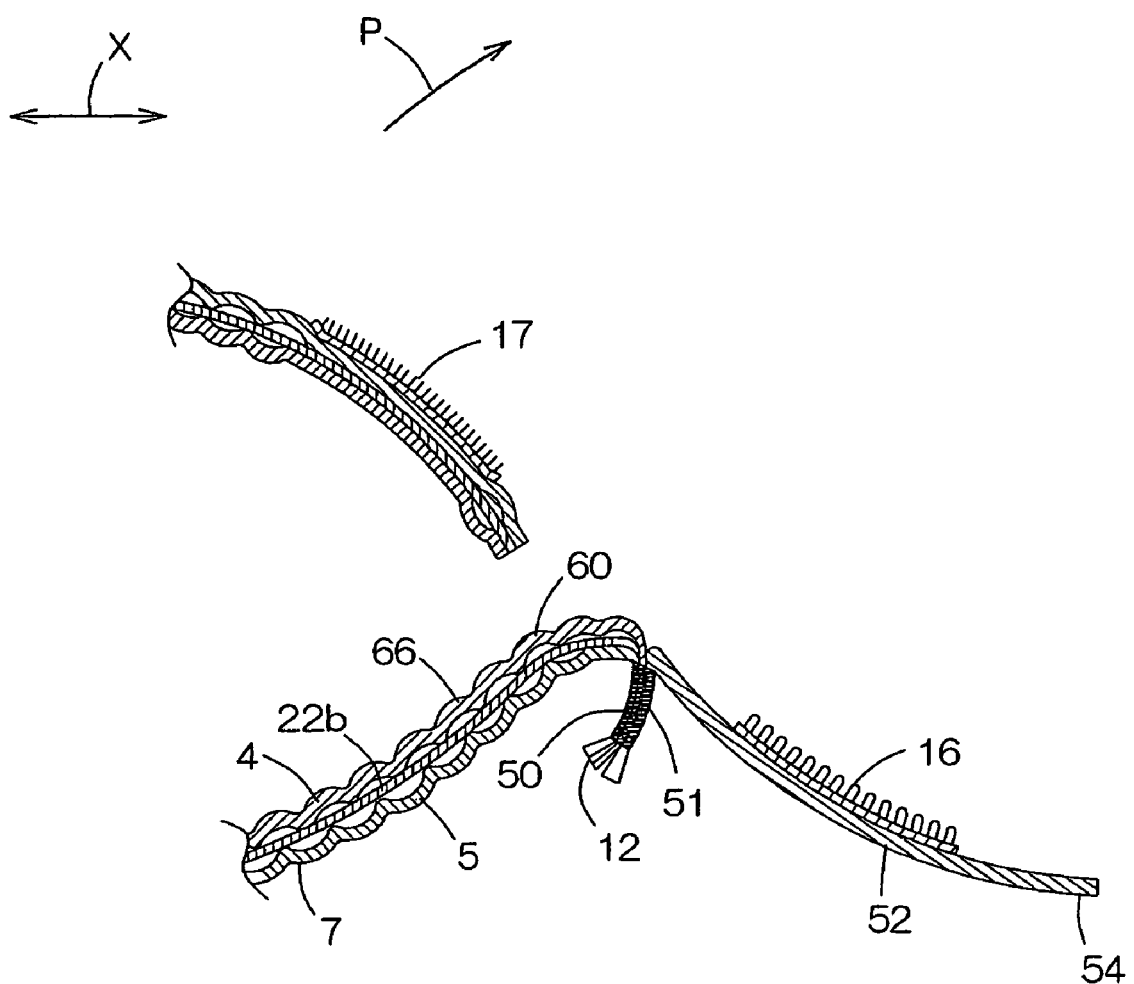
FIG. 4 is a view similar to FIG. 3, showing the disposable diaper with flaps turned around outward.

FIG. 4 is a view similar to FIG. 3, showing the flap-like section 52 had been separated from the hook member 17 as shown by FIG. 3 have been further rotated in the direction P. In regions 60 defined immediately inside the zones 50 of the rear waist region 7 as viewed in the transverse direction, the inner sheet 4, the outer sheet 5 and the second elastic members 22b forming together the rear waist region are bonded one another intermittently in the transverse direction X and contraction of these second elastic members 22b for the rear waist region forms the gathers 66 repetitively undulating in the transverse direction X, i.e., between the opposite side edges 12, 12. Rigidity which resists against bending of the flap-like sections 52 in the transverse direction Z is set to be higher than rigidity which stands against bending of the regions 60 defined immediately inside the zones 50. Such uniquely differentiated of the rigidity ensures that the regions 60 defined immediately inside the respective zones 50, formed with the gathers 66 and having relatively low rigidity can easily bow as the flap-like sections 52 are turned around in the direction P. Consequentially, even the finger-grips 54 are out of the fingers after the flap-like sections 52 have been turned around so as to extend from the inside to the outside in the transverse direction X as shown, these flap-like sections 52 are able to maintain such state turned around outward. Such state of the flap-like sections corresponds to the state thereof as seen in FIG. 2.

When the diaper 1 is put on a baby in side lying position or face-up position, the flap-like sections 52 of this diaper 1 can be easily turned around outward in the transverse direction of the diaper 1 under the influence of the regions 60 defined immediately inside the respective zones 50. Consequentially, it is ensured that the finger-grips 54 of the respective flap-like sections 52 can be easily caught by the fingers in comparison with the case of the well known diaper 1 of which the flap-like sections 52 continue to extend inward in the transverse direction of the diaper.

Figure 5:
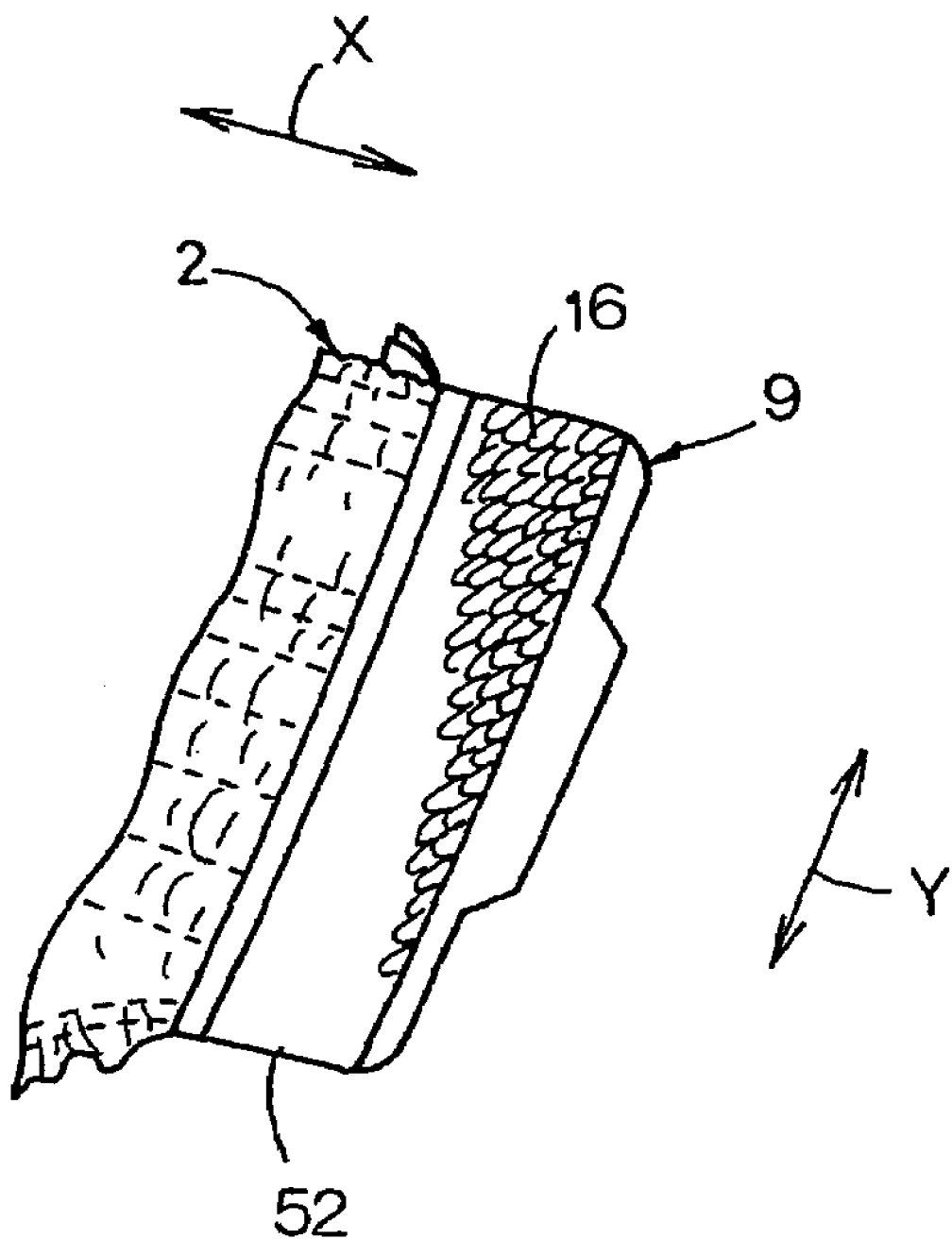
FIG. 5 is a fragmentary view of one preferred embodiment of the diaper according to the present invention.
Figure 6:
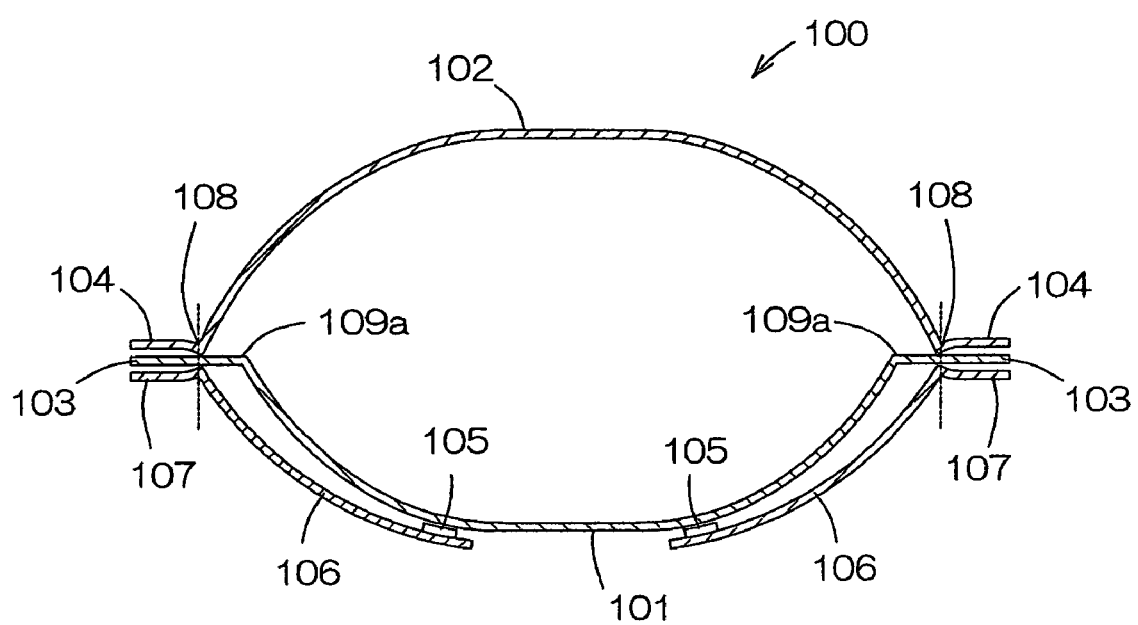
FIG. 6 is a sectional view showing one example of the well known diapers.
Figure 7:
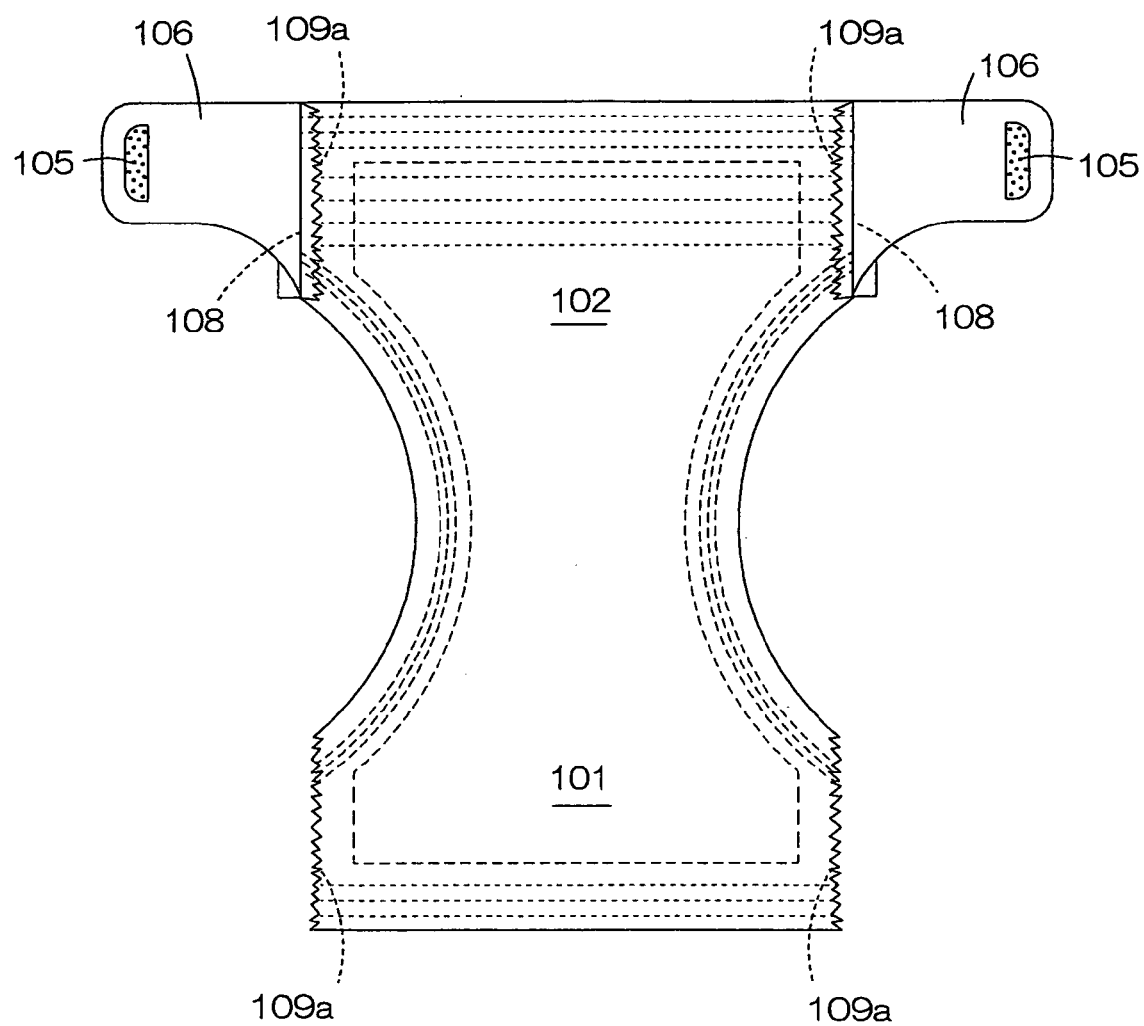
FIG. 7 is a developed plan view showing the well known diaper converted to the open-type.

FIG. 5 is a fragmentary view showing one preferred embodiment of the diaper 1 according to the present invention. This alternative embodiment of the diaper 1 similar to the previously described embodiment of the diaper 1 so far as the flap-like section 52 is dimensioned identically to that in the diaper 1 previously described in reference with FIG. 2 but distinguished from the previous described diaper 1 in that the loop member 16 is attached to the associated flap-like section 52 so as to extend in the longitudinal direction Y over the entire area of the flap-like section 52. Compared to the case in which the loop member 16 has a dimension as measured in the longitudinal direction Y is smaller than that of the flap-like section 52 in the corresponding direction as in the connector sheet strips 9 shown by FIG. 2, a larger area exhibiting high rigidity is obtained. This arrangement advantageously further facilitates the flap-like sections 52 to be turned around outward in the transverse direction of the diaper 1.

Without departing from the scope of the invention, it is possible to attach the connector sheet strips 9 of FIG. 1 not to the rear waist region 7 but to the front waist region 6 so that the gathers 66 formed by the front waist region 6 may facilitate the flap-like sections 52 to be turned around outward in the transverse direction of the diaper 1. It is also possible without departing from the scope of the invention to attach the loop member 16 to the front waist region 6 and to attach the hook members 17 to the associated connector sheet strip 9 vice versa with respect to the embodiment shown by FIG. 1. It is further possible without departing from the scope of the invention to provide on the inner surfaces 9a of the respective flap-like sections 52 with pressure-sensitive adhesive layers serving as fastening means to the front waist region 6 and to provide the outer sheet 5 of the front waist region 6 with a target zone onto which those pressure-sensitive adhesive layers can be releasably anchored.

While the diaper 1 for baby has been described in reference with the accompanying drawings, the present invention may be implemented also in the various forms, for example, of disposable diaper for adult, disposable diaper for incontinent patient and disposable diaper comprising the bodily fluid absorbent core 34, instead of the bodily fluid absorbent panel 3, sandwiched between the liquid-pervious inner sheet 4 and the liquid-impervious outer sheet 5. Furthermore, the present invention may be implemented in the form of training pants, diaper cover or wearing article used to hold a urine retention pad both without the bodily fluid absorbent panel 3, or the like.

The present invention makes it possible to manufacture the disposable wearing article requiring no troublesome handling to put it on the wearing body.

The entire discloses of Japanese Patent Application No. 2005-12078 filed on Jan. 19, 2005 including specification, drawings and abstract are herein incorporated by reference in its entirety.

What is claimed is:

1. A disposable wearing article having a longitudinal direction and a transverse direction orthogonal to each other, said article comprising:
a front waist region;
a rear waist region;
a crotch region;
each of said regions having a pair of side edges opposed to each other in said transverse direction, and opposite inner and outer surfaces, the inner surface being adapted to face a wearer's skin in use and the outer surface being adapted to face away from the wearer's skin in use;
connector sheet strips attached to one of said front and rear waist regions in a vicinity of the associated side edges; and
elastic members attached in stretched state to said one waist region so as to be contractible in the transverse direction;
said one waist region being formed with gathers and undulating in said transverse direction between said side edges under contraction of said elastic members;
each of said connector sheet strips respectively comprising:
a proximal section fixed to the inner surface of said one waist region in the vicinity of one of said associated side edges;
a flap section moveable between a first position where said flap section extends in the transverse direction inward from said proximal section and a second position where said flap section extends in the transverse direction outward from said proximal section, said flap section having a surface that is opposed to said inner surface of said one waist region when the flap section is in the first position; and
a fastening element provided on said surface of said flap section and releasably engageable with the outer surface of the other waist region;
wherein said one waist region has zones immediately adjacent bonding sites where the proximal sections of the connector sheet strips are bonded to the respective side edges of said one waist region, said zones being located inboard of the adjacent bonding sites and formed with said gathers; and
wherein a flexural rigidity of each said flap section as measured in said transverse direction is higher than that of said one waist region as measured in said zones.

2. The article of claim 1, wherein said zones are deformed due to the lower flexural rigidity when the respective flap sections are unfolded from the first position to the second position.

3. The article of claim 1, wherein said fastening elements are loops.

4. The article of claim 3, wherein said loops cover an entire longitudinal extent of the respective flap section.

5. The article of claim 4, wherein each said zone comprises multiple layers and yet has a lower flexural rigidity than the associated flap section.

6. The article of claim 5, wherein the multiple layers of each said zone comprise a topsheet and a backsheet defining the inner and outer surfaces, respectively, of said one waist region.

7. The article of claim 6, wherein the multiple layers of said zones further comprise said elastic members.

8. The article of claim 6, wherein the bonding sites comprise materials of said topsheet, backsheet and connector sheet strips in molten and solidified state.

9. The article of claim 1, wherein each said zone comprises multiple layers and yet has a lower flexural rigidity than the associated flap section.

10. The article of claim 9, wherein the multiple layers of each said zone comprise a topsheet and a backsheet defining the inner and outer surfaces, respectively, of said one waist region.

11. The article of claim 10, wherein the multiple layers of said zones further comprise said elastic members.

12. The article of claim 10, wherein the bonding sites comprise materials of said topsheet, backsheet and connector sheet strips in molten and solidified state.

* * * * *